(12) United States Patent
Flagler et al.

(10) Patent No.: US 6,358,877 B1
(45) Date of Patent: Mar. 19, 2002

(54) METAL CATALYSTS COMPLEXED WITH SULFONE OR SULFOXIDE COMPOUNDS

(75) Inventors: Kendra L. Flagler, Fenelon Falls; David E. Laycock, Ontario, both of (CA)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/574,846

(22) Filed: May 19, 2000

Related U.S. Application Data

(60) Provisional application No. 60/153,086, filed on Sep. 10, 1999.

(51) Int. Cl.$^7$ .......................... B01J 27/26; B01J 27/02; B01J 31/16; B01J 31/22
(52) U.S. Cl. ................. 502/175; 502/150; 502/152; 502/153; 502/155; 502/162; 502/168; 502/200; 502/216; 525/403; 525/419; 526/108; 526/113; 526/120; 526/135; 526/140; 526/273; 528/90; 528/92; 528/103
(58) Field of Search ................. 502/150, 152, 502/153, 155, 162, 168, 175, 200, 216; 525/403, 409; 526/120, 108, 113, 135, 140, 273; 528/90, 92, 103

(56) References Cited

U.S. PATENT DOCUMENTS

| | | | |
|---|---|---|---|
| 3,278,457 A | 10/1966 | Milgrom | |
| 3,404,109 A | 10/1968 | Milgrom | |
| 3,427,256 A | 2/1969 | Milgrom | |
| 5,158,922 A | 10/1992 | Hinney et al. | |
| 5,470,813 A | 11/1995 | Le-Khac | 502/175 |
| 5,482,908 A | 1/1996 | Le-Khac | 502/156 |
| 5,589,431 A | 12/1996 | Le-Khac | 502/175 |

FOREIGN PATENT DOCUMENTS

| | | |
|---|---|---|
| EP | 0 743 093 | 11/1996 |
| EP | 0 862 947 | 9/1998 |

OTHER PUBLICATIONS

EP 862947 Derwent Abstract, Sep. 1998.

*Primary Examiner*—Elizabeth D. Wood

(57) ABSTRACT

Metal cyanide catalysts are complexed with organic sulfone or sulfoxide compounds. The catalysts are active alkylene oxide polymerization catalysts that tend to have short induction periods and moderate exotherms.

16 Claims, No Drawings

METAL CATALYSTS COMPLEXED WITH SULFONE OR SULFOXIDE COMPOUNDS

CROSS-REFERENCE TO RELATED APPLICATIONS

This application claims the benefit of provisional application 60/153,086, filed Sep. 10, 1999, which is incorporated by reference in its entirety.

BACKGROUND OF THE INVENTION

This invention relates to metal catalysts for alkylene oxide polymerization.

Alkylene oxides such as ethylene oxide, propylene oxide and 1,2-butylene oxide are polymerized to form a wide variety of polyether products. For example, polyether polyols are prepared in large quantities for polyurethane applications. Other polyethers are used as lubricants, brake fluids, compressor fluids, and many other applications.

These polyethers are commonly prepared by polymerizing one or more alkylene oxides in the presence of an initiator compound and an alkali metal catalyst. The initiator compound is typically a material having one or more hydroxyl, primary or secondary amine, carboxyl or thiol groups. The function of the initiator is to set the nominal functionality (number of hydroxyl groups/molecule) of the product polyether, and in some instances to incorporate some desired functional groups into the product.

Until recently, the catalyst of choice was an alkali metal hydroxide such as potassium hydroxide. Potassium hydroxide has the advantages of being inexpensive, adaptable to the polymerization of various alkylene oxides, and easily recoverable from the product polyether.

However, to a varying degree, alkali metal hydroxides catalyze an isomerization of propylene oxide to form allyl alcohol. Allyl alcohol acts as a monofunctional initiator during the polymerization of propylene oxide. Thus, when potassium hydroxide is used to catalyze propylene oxide polymerizations, the product contains allyl alcohol-initiated, monofunctional impurities. As the molecular weight of the product polyether increases, the isomerization reaction becomes more prevalent. Consequently, poly(propylene oxide) products having equivalent weights of about 800 or more tend to have very significant quantities of the monofunctional impurities when prepared using KOH as the catalyst. This tends to reduce the average functionality and broaden the molecular weight distribution of the product.

More recently, the so-called double metal cyanide (DMC) catalysts have been used commercially as polymerization catalysts for alkylene oxides. These DMC catalysts are described, for example, in U.S. Pat. Nos. 3,278,457, 3,278,458, 3,278,459, 3,404,109, 3,427,256, 3,427,334, 3,427,335 and 5,470,813, among many others. Those DMC catalysts that are active usually do not significantly promote the isomerization of propylene oxide, polyethers having low unsaturation values and higher molecular weights can be prepared, compared to potassium hydroxide-catalyzed polymerizations. Recently, developmental and commercial efforts have focused almost exclusively on zinc hexacyanocobaltate, together with a specific completing agent, t-butanol.

As described in U.S. Pat. No. 5,470,813, one disadvantage of DMC catalysts is that they tend to require an induction period of close to an hour to many hours in some cases before becoming active. Little polymerization occurs during this induction period, but it is followed by a strongly exothermic reaction. For some operations, it would be desirable to reduce this induction period and to provide a less strongly exothermic reaction.

It would be desirable, therefore, to provide an active catalyst for polymerizing alkylene oxides that exhibits a short induction period before rapidly polymerizing alkylene oxides, and provides for a more controlled exotherm when the rapid polymerization commences.

SUMMARY OF THE INVENTION

In one aspect, this invention is a metal cyanide catalyst complexed with an organic sulfone ($R^5$—$S(O)_2$—$R^5$) or sulfoxide ($R^5$—$S(O)$—$R^5$) compound.

In another aspect, this invention is an improvement in a process for polymerizing an epoxide compound in the presence of a catalyst, the improvement wherein the catalyst is a metal cyanide catalyst complexed with an organic sulfone or sulfoxide compound.

It has been found that the metal cyanide catalyst complex of the invention has excellent activity as an epoxide polymerization catalyst. In particular, the catalyst often exhibits sharply reduced induction periods when used in such polymerizations, compared, for example, to the zinc hexacyanocobaltate/t-butanol/poly(propylene oxide) complex that is most commonly used. In addition, smaller, more easily controlled exotherms are usually seen when rapid alkylene oxide polymerization begins.

DETAILED DESCRIPTION OF THE INVENTION

By "metal cyanide catalyst", it is meant a catalyst represented by the formula

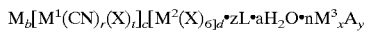

wherein

M is a metal ion that forms an insoluble precipitate with the $M^1(CN)_r(X)_t$ group and which has at least one water soluble salt;

$M^1$ and $M^2$ are transition metal ions that may be the same or different;

each X independently represents a group other than cyanide that coordinates with an $M^1$ or $M^2$ ion;

$M^3_x A_y$ represents a water-soluble salt of metal ion $M^3$ and anion A, wherein $M^3$ is the same as or different than M;

L represents the organic sulfone or sulfoxide compound;

b and c are positive numbers that, together with d, reflect an electrostatically neutral complex;

d is zero or a positive number;

x and y are numbers that reflect an electrostatically neutral salt;

r is from 4 to 6; t is from 0 to 2; and a and n are positive numbers (which may be fractions) indicating the relative quantities of water sulfone or sulfoxide compound, and $M^3_x A_y$, respectively.

The X groups in any $M^2(X)_6$ do not have to be all the same. The molar ratio of c:d is advantageously from about 100:0 to about 20:80, more preferably from about 100:0 to about 50:50, and even more preferably from about 100:0 to about 80:20.

Similarly, mixtures of two or more different $M^1(CN)_r(X)_t$ groups can be used.

M and $M^3$ are preferably metal ions selected from the group consisting of $Zn^{+2}$, $Fe^{+2}$, $Co^{+2}$, $Ni^{+2}$, $Mo^{+4}$, $Mo^{+6}$, $Al^{+3}$, $V^{+4}$, $V^{+5}$, $Sr^{+2}$, $W^{+4}$, $W^{+6}$, $Mn^{+2}$, $Sn^{+2}$, $Sn^{+4}$, $Pb^{+2}$, $Cu^{+2}$, $La^{+3}$ and $Cr^{+3}$. M and $M^3$ are more preferably $Zn^{+2}$, $Fe^{+2}$, $Co^{+2}$, $Ni^{+2}$, $La^{+3}$ and $Cr^{+3}$. M is most preferably $Zn^{+2}$.

$M^1$ and $M^2$ are preferably $Fe^{+3}$, $Fe^{+2}$, $Co^{+3}$, $Co^{+2}$, $Cr^{+2}$, $Cr^{+3}$, $Mn^{+2}$, $Mn^{+3}$, $Ir^{+3}$, $Ni^{+2}$, $Rh^{+3}$, $Ru^{+2}$, $V^{+4}$ and $V^{+5}$. Among the foregoing, those in the plus-three oxidation state are more preferred. $Co^{+3}$ and $Fe^{+3}$ are even more preferred and $Co^{+3}$ is most preferred. $M^1$ and $M^2$ may be the same or different.

Preferred groups X include anions such as halide (especially chloride), hydroxide, sulfate, carbonate, late, thiocyanate, isocyanate, isothiocyanate, $C_{1-4}$ carboxylate and nitrite ($NO_2-$), and uncharged species such as CO, $H_2O$ and NO. Particularly preferred groups X are NO, $NO_2-$ and CO.

r is preferably 5 or 6, most preferably 6 and t is preferably 0 or 1, most preferably 0. In most instances, r+t will equal 6.

Suitable anions A include halides such as chloride and bromide, nitrate, sulfate, carbonate, cyanide, oxalate, thiocyanate, isocyanate, isothiocyanate, perchlorate and $C_{1-4}$ carboxylate. Chloride ion is especially preferred.

L represents an organic sulfone or sulfoxide compound. Suitable sulfone compounds are represented by the general formula $R^5$—$S(O)_2$—$R^5$, where each $R^5$ is unsubstituted or inertly substituted alkyl, cycloalkyl, aryl, or, together with the other $R^5$, forms part of a ring structure that includes the sulfur atom of the sulfone (—$S(O)_2$—) group. Suitable sulfoxide compounds are represented by the general formula $R^5$—$S(O)$—$R^5$, where each $R^5$ is as just described. In this context, "inertly substituted" means that the group contains no substituent which undesirably reacts with the metal cyanide compound, its precursor compounds (as described below) or an alkylene oxide, or which otherwise undesirably interferes with the polymerization of an alkylene oxide. Examples of such inert substituents include ether, alkoxyl, hydroxyl, nitrite, aldehyde, ketone, amide, sulfide, additional sulfone or sulfoxide groups, and the like. Each $R^5$ is preferably unsubstituted and is also preferably either an alkyl group or, together with the other $R^5$, forms part of a ring structure that includes the sulfone or sulfoxide group. Especially preferred $R^5$ groups are 1–4 carbon atom alkyl groups or those that together form a 5–8 member ring with the sulfur atom of the sulfone or sulfoxide groups. More preferred compounds are water-soluble, including for example, dimethyl sulfoxide (DMSO), tetramethylene sulfoxide, 2,2-sulfonyl diethanol, dimethyl sulfone and sulfolane (tetramethylene sulfone). DMSO is the most preferred compound, because it exhibits particularly short induction periods in initiated propylene oxide polymerization.

The sulfone or sulfoxide compound is generally and preferably the sole completing agent.

The catalyst complex is conveniently made by first dissolving or dispersing a water-soluble metal cyanide compound in an inert solvent such as water or methanol. Mixtures of two or more metal cyanide compounds can be used. The water-soluble metal cyanide compound is represented by the general formula $B_u[M^1(CN)_r(X)_t]_v$, in which B is hydrogen or a metal that forms a water-soluble salt with the $[M^1(CN)_r(X)_t]$ ion, u and v are integers that result in an electrostatically neutral compound and $M^1$, X, r and t are as described before. B is preferably hydrogen, sodium or potassium. Compounds in which B is hydrogen are conveniently formed by passing an aqueous solution of the corresponding alkali metal salt through a cation-exchange resin that is in the hydrogen form.

In addition, the solution or dispersion of the metal cyanide compound may also contain compounds that have the structure $B_u[M^2(X)_6]_v$, wherein $M^2$ is a transition metal and X, B, u and v are as before. $M^2$ may be the same as or different from $M^1$.

The solution or dispersion is then combined the resulting solution(s) with an aqueous solution of a water soluble metal salt, in the presence of the sulfone or sulfoxide compound. The metal salt is represented by the general formula $M_xA_y$, where M, A, x and y are as defined before. Especially suitable metal salts include zinc halides, zinc hydroxide, zinc sulfate, zinc carbonate, zinc cyanide, zinc oxalate, zinc thiocyanate, zinc isocyanate, zinc $C_{1-4}$ carboxylates, and zinc nitrate. Zinc chloride is most preferred.

The temperature of mixing is not critical, provided that the starting materials remain in solution or well dispersed until the mixing is performed. Temperatures of about 10 to about the boiling point of the inert solvent, particularly 15–40° C., are most suitable. The mixing can be done with rapid agitation. Intimate mixing techniques as are described in U.S. Pat. No. 5,470,813 can be used, but are not necessary.

In precipitating the catalyst, at least enough metal salt is used to provide one equivalent of metal ion (M) for each equivalent of metal cyanide ion ($M^1(CN)_r(X)_t$), plus each equivalent of $M^2(X)_6$ ion, if used. It has been found that in general, more active catalysts are those prepared using an excess of the metal salt. This excess metal is believed to exist in the catalyst complex as a salt in the form $M_xA_y$ or $M^3_xA_y$. This excess metal salt can be added in the precipitation step, such as by adding up to about three equivalents of metal salt, preferably from about 1.1 to about 3, more preferably about 1.5 to about 2.5 equivalents of metal salt, per combined equivalents of metal cyanide ion plus any $M^2(X)_6$ ions.

An alternate way to add the excess metal salt is to do so in a separate step following the precipitation step, as described more fully below. The metal ion in excess salt may be different than that in the metal salt used to precipitate the catalyst.

It is preferred to add the solution of the metal cyanide compound to that of the metal salt, and it is also preferred that the mixing be done with agitation. Agitation is preferably continued for a period after the mixing is completed. The metal cyanide catalyst precipitates and forms a dispersion in the supernatant fluid.

The catalyst complex may be precipitated by mixing the solution or dispersion of the metal salt with the solution or dispersion of the metal cyanide compound in the presence of the sulfone or sulfoxide compound. One way of doing this is to add the sulfone or sulfoxide compound to the solution or dispersion of the metal cyanide compound before the solutions are mixed. Alternately, both starting solutions or dispersions may be added simultaneously with the sulfone or sulfoxide compound. A third way is to mix the starting solutions or dispersions, followed immediately by adding the sulfone or sulfoxide compound. After adding this initial amount of sulfone or sulfoxide compound, the mixture is generally stirred for several minutes to allow the desired catalyst complex to form and precipitate.

The resulting precipitated catalyst complex is then recovered by a suitable technique such as filtration or centrifugation. Preferably, the catalyst complex is subjected to one or more subsequent washings with water, sulfone or sulfoxide compound, polyether polyol (when used) or some combination thereof. This is conveniently done by re-slurrying the catalyst in the liquid with agitation for several minutes and filtering. Washing is preferably continued at least until essentially all unwanted ions, particularly alkali metal and halide ions, are removed from the complex.

It has been found that catalyst preparation is sometimes easier if the catalyst is treated with a polyether polyol of a molecular weight of about 300–4000. When a polyether polyol is used in the catalyst complex, it can be added with the initial amount of sulfone or sulfoxide compound, or in one or more subsequent washings of the complex.

The final catalyst complex is conveniently dried, preferably under vacuum and moderately elevated temperatures (such as from about 50–60° C.) to remove excess water and volatile organics. Drying is preferably done until the catalyst complex reaches a constant weight.

In an alternative technique for forming the catalyst complex, an aqueous solution containing only a stoichiometric amount of metal salt in relation to the combined amount of metal cyanide compound (and any $M^2(X)_6$ compound that is used) is used in the initial mixing and precipitation step. After this initial precipitation is complete, the precipitate is washed with water to remove unwanted ions. The precipitate is then combined with a small amount of a solution containing water, additional metal salt, and the sulfone or sulfoxide compound. The metal salt used may the same as that used in forming the precipitate, or may be a salt of a different metal. The amount of this added solution is preferably that amount which is absorbed by the precipitate. A typical amount of solution to be used is from about 0.5 to about 2, preferably about 0.8 to about 1.5, more preferably about 1 to about 1.5 milliliters of solution per gram of isolated precipitate. The amount of metal salt added with this solution is advantageously about 9 to about 30, preferably about 11 to about 25, parts by weight per 100 parts by weight of the isolated precipitate. The sulfone or sulfoxide compound is advantageously present in a weight ratio of about 90:10 to about 10:90, preferably about 70:30 to about 30:70, with the water. If desired, a polyether polyol can be included in the solution. The resulting catalyst complex can be dried and used without further treatment, or may be subjected to additional washings with water as before, although it is preferred not to perform additional washings with sulfone compound, sulfoxide compound or polyether polyol.

The catalyst complex of the invention is used to polymerize alkylene oxides to make polyethers. In general, the process includes mixing a catalytically effective amount of the catalyst with an alkylene oxide under polymerization conditions, and allowing the polymerization to proceed until the supply of alkylene oxide is essentially exhausted. The concentration of the catalyst is selected to polymerize the alkylene oxide at a desired rate or within a desired period of time. Generally, a suitable amount of catalyst is from about 5 to about 10,000 parts by weight metal cyanide catalyst per million parts combined weight of alkylene oxide, and initiator and comonomers, if present. More preferred catalyst levels are from about 10, especially from about 25, to about 1000, more preferably about 250 ppm, on the same basis.

To control molecular weight, impart a desired functionality (number of hydroxyl groups/molecule) or a desired terminal functional group, an initiator compound as described before is preferably mixed with the catalyst complex at the beginning of the reaction. Suitable initiator compounds include monoalcohols such methanol, n-propanol, isopropanol, n-butanol, isobutanol, t-butanol, octanol, octadecanol, 3-butyn-1-ol, 3-butene-1-ol, propargyl alcohol, 2-methyl-2-propanol, 2-methyl-3-butyn-2-ol, 2-methyl-3-butene-2-ol, 3-butyn-1-ol, 3-butene-1-ol and the like. The suitable monoalcohol initiator compounds include halogenated alcohols such as 2-chloroethanol, 2-bromoethanol, 2-chloro-1-propanol, 3-chloro-1-propanol, 3-bromo-1-propanol, 1,3-dichloro-2-propanol, 1-chloro-2-methyl-2-propanol as well as nitroalcohols, keto-alcohols, ester-alcohols, cyanoalcohols, and other inertly substituted alcohols. Suitable polyalcohol initiators include ethylene glycol, propylene glycol, glycerine, 1,1,1-trimethylol propane, 1,1,1-trimethylol ethane, 1,2,3-trihydroxybutane, pentaerythritol, xylitol, arabitol, mannitol, 2,5-dimethyl-3-hexyn-2,5-diol, 2,4,7,9-tetramethyl-5-decyne-4,7-diol, sucrose, sorbitol, alkyl glucosides such a methyl glucoside and ethyl glucoside and the like. Low molecular weight polyether polyols, particularly those having an equivalent weight of about 350 or less, more preferably about 125–250, are also useful initiator compounds.

Among the alkylene oxides that can be polymerized with the catalyst complex of the invention are ethylene oxide, propylene oxide, 1,2-butylene oxide, styrene oxide, and mixtures thereof Various alkylene oxides can be polymerized sequentially to make block copolymers. More preferably, the alkylene oxide is propylene oxide or a mixture of propylene oxide and ethylene oxide and/or butylene oxide. Especially preferred are propylene oxide alone or a mixture of at least 50 weight % propylene oxide and up to about 50 weight % ethylene oxide.

In addition, monomers that will copolymerize with the alkylene oxide in the presence of the catalyst complex can be used to prepare modified polyether polyols. Such comonomers include oxetanes as described in U.S. Pat. Nos. 3,278,457 and 3,404,109, and anhydrides as described in U.S. Pat. Nos. 5,145,883 and 3,538,043, which yield polyethers and polyester or polyetherester polyols, respectively. Hydroxyalkanoates such as lactic acid, 3-hydroxybutyrate, 3-hydroxyvalerate (and their dimers), lactones and carbon dioxide are examples of other suitable monomers that can be polymerized with the catalyst of the invention.

The polymerization reaction typically proceeds well at temperatures from about 25 to about 150° C., preferably from about 80–130° C. A convenient polymerization technique involves mixing the catalyst complex and initiator, and pressuring the reactor with the alkylene oxide. After a short induction period, polymerization proceeds, as indicated by a loss of pressure in the reactor. Once the polymerization has begun, additional alkylene oxide is conveniently fed to the reactor on demand, until enough alkylene oxide has been added to produce a polymer of the desired equivalent weight.

Another convenient polymerization technique is a continuous method. In such continuous processes, an activated initiator/catalyst mixture is continuously fed into a continuous reactor such as a continuously stirred tank reactor (CSTR) or a tubular reactor. A feed of alkylene oxide is introduced into the reactor and the product continuously removed.

The catalyst of this invention is especially useful in making propylene oxide homopolymers and random copolymers of propylene oxide and up to about 15 weight percent ethylene oxide (based on all monomers). The polymers of particular interest have a hydroxyl equivalent weight of from about 800, preferably from about 1000, to about 5000, preferably about 4000, more preferably to about 2500, and unsaturation of no more than 0.02 meq/g, preferably no more than about 0.01 meq/g.

The product polymer may have various uses, depending on its molecular weight, equivalent weight, functionality and the presence of any functional groups. Polyether polyols so made are useful as raw materials for making polyurethanes.

Polyethers can also be used as surfactants, hydraulic fluids, as raw materials for making surfactants and as starting materials for making aminated polyethers, among other uses.

The following examples are provided to illustrate the invention, but are not intended to limit its scope. All parts and percentages are by weight unless otherwise indicated.

EXAMPLE 1

A. Catalyst preparation

A solution of potassium hexacyanocobaltate (8.0 g, 0.024 mol) in 140 mL of distilled water is prepared. It is added to a stirred solution of 25 g (0.18 mol) of zinc chloride in 40 mL water. A solution of 100 mL dimethyl sulfoxide (DMSO) in 100 mL water is immediately added, and the resulting mixture stirred for 10 minutes. A slurry forms, which is filtered through a Buchner funnel. The collected solids are reslurried in a solution containing 60 mL water and 140 mL DMSO, stirred 10 minutes and filtered as before. The solids are then reslurried in 200 mL DMSO, stirred for 10 minutes and filtered again. The solids are vacuum dried for 18 hours at 50° C.

B. Initiated elevated temperature polymerization 30 grams of a 700 MW polyether triol and 0.2 grams of the catalyst complex from part A are mixed in a Parr reactor. After purging with nitrogen, the mixture is heated to 100° C. and pressurized to 50 psig with propylene oxide. Polymerization begins immediately, but no measurable exotherm is seen. As the polymerization proceeds, propylene oxide is continuously fed to the reactor to maintain the pressure at 50 psig, until a total of 140 g propylene oxide are added. The polymerization of the entire loading of propylene oxide takes about three hours. The unsaturation level of the resulting polyether polyol is 0.013 meq/g, and the polydispersity is about 1.29.

EXAMPLE 2

A. Catalyst Preparation

A solution of 4.1 g sodium nitroferricyanide in 50 mL deionized water is passed through a column of 25 g a macroporous styrene-divinylbenzene strong acid cation exchange resin Dowex MSC-1, available from The Dow Chemical Company) in the hydrogen form. The eluent (containing 0.014 moles $H_2[Fe(CN)_5(NO)]$) is added to another solution of 4.5 g potassium hexacyanocobaltate (0.014 moles) in 50 mL deionized water. The mixture is then added to a stirred solution of 25 g zinc chloride in 40 mL deionized water. This is followed by immediately adding 200 mL of a 50/50 by volume solution of water and DMSO. The resulting slurry is homogenized for 10 minutes and poured into a large, stirred beaker. To it is added a solution of 200 mL water, 2 mL of DMSO and 2 g of a 4000 molecular weight, nominally trifunctional poly(propylene oxide), followed by stirring for three minutes. The slurry is then filtered through a Buchner funnel to isolate the solids. The solids are reslurried in a solution containing 60 mL water, 140 mL DMSO and 2 g of the same poly(propylene oxide), stirred 10 minutes and filtered as before. The resulting solids are then reslurried again in a solution of 200 mL DMSO and 1 g of the poly(propylene oxide), stirred another 10 minutes, and filtered. The product is then vacuum dried overnight at 50° C.

B. Initiated elevated temperature polymerization.

An elevated temperature polymerization is conducted as described in Example 1B. After a 10–15 minute induction period, polymerization begins, accompanied by an exotherm of 20° C. The unsaturation level of the resulting polyether polyol is 0.009 meq/g, and the polydispersity is 1.26.

EXAMPLE 3

A. Catalyst Preparation

A solution of 25 g zinc chloride in 40 mL deionized water is added with mixing to solution of 8.0 g potassium hexacyanocobaltate in 140 mL water. The mixture is stirred for several seconds. Then a solution of 20 g methyl sulfone in 200 mL water is added. The mixture is stirred for 10 minutes and vacuum filtered. The filter cake is reslurried in a solution of 25 g methyl sulfone in 180 mL water, and 1 g of a 450 molecular weight trifunctional poly(propylene oxide) is added. The mixture is stirred 10 minutes and filtered again. The filter cake is then reslurried a second time under the same conditions and once again filtered. The product is then vacuum dried at 85° C. for 24 hours. It is then slurried in acetone, centrifuged to recover the solids, and dried under vacuum for 18 hours at 100° C.

B. Initiated elevated temperature polymerization

In a Parr reactor are mixed 30 grams of a 700 MW polyether triol and enough of the catalyst complex from part A to provide about 1000 ppm catalyst, based on expected product weight. After purging with nitrogen, the mixture is heated to 100° C. and pressurized to 50 psig with propylene oxide. After an induction period of about 16 minutes, polymerization begins and a very slight (5° C.) exotherm is seen. As the polymerization proceeds, propylene oxide is continuously fed to the reactor to maintain the pressure at 35 psig, until a total of 123 g propylene oxide are added. The polymerization of the entire loading of propylene oxide takes about twenty-five minutes. The unsaturation of the resulting polymer is 0.002 meq/g.

EXAMPLE 4

A. Catalyst Preparation

A solution of 6.25 g zinc chloride in 10 mL deionized water is added with mixing to solution of 2.0 g potassium hexacyanocobaltate in 35 mL water. The mixture is stirred for several seconds. Then 20 mL of a 50/50 by volume mixture of tetramethylene sulfoxide and distilled water is added. The mixture is stirred for 10 minutes and filtered. The filter cake is reslurried in a solution of 12 mL methyl sulfone and 1 g of a 450 molecular weight trifunctional poly (propylene oxide) and filtered again. The filter cake is then dissolved in acetone, filtered to recover the solids, and dried under vacuum for 7 hours at 85° C.

B. Initiated elevated temperature polymerization

The catalyst from part A is evaluated for activity as described in Example 3B. After an induction period of about 25 minutes, polymerization begins and a slight (24° C.) exotherm is seen. The polymerization of the entire loading of propylene oxide takes about twenty-six minutes. The unsaturation of the resulting polymer is 0.007 meq/g.

EXAMPLE 5

A. Catalyst Preparation

A solution of 6.25 g zinc chloride in 10 mL deionized water is added with mixing to solution of 2.0 g potassium hexacyanocobaltate in 35 mL water. The mixture is stirred for several seconds. Then 20 mL of a 50/50 by volume mixture of 2,2-sulfonyl diethanol and distilled water is added. The mixture is stirred for 10 minutes and filtered. The filter cake is reslurried in a solution of 15 mL of 2,2-sulfonyl diethanol, 10 mL deionized water and 2 g of a 450 molecular weight trifunctional poly(propylene oxide), stirred 10 minutes and filtered again. The filter cake is reslurried a second time in a solution of 2,2-sulfonyl diethanol (37.5 mL) and 0.93 g of the poly(propylene oxide). The filter cake is then dissolved in acetone, filtered to recover the solids, and dried under vacuum for 18 hours at 85° C.

B. Initiated elevated temperature polymerization

The catalyst from part A is evaluated for activity as described in Example 3B, using 0.19 g of the catalyst. Polymerization begins immediately. No measurable exotherm is seen as the propylene oxide polymerizes. The polymerization of the entire loading of propylene oxide takes about 103 minutes.

What is claimed is:

1. A metal cyanide catalyst complexed with an organic sulfone or sulfoxide compound.

2. The catalyst of claim 1 which is complexed with an organic sulfone represented by the general structure $R^5$—$S(O)_2$—$R^5$ wherein each $R^5$ is independently an unsubstituted or inertly substituted alkyl group, cycloalkyl, aryl, or, together with the other $R^5$, forms part of a ring structure that includes the sulfur atom of the sulfone group.

3. The catalyst of claim 2 wherein the metal cyanide catalyst is represented by the general structure

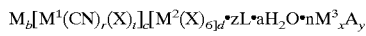

wherein

M is a metal ion that forms an insoluble precipitate with the $M^1(CN)_r(X)_t$ group and which has at least one water soluble salt;

$M^1$ and $M^2$ are transition metal ions that may be the same or different;

each X independently represents a group other than cyanide that coordinates with an $M^1$ or $M^2$ ion;

$M^3_xA_y$ represents a water-soluble salt of metal ion $M^3$ and anion A, wherein $M^3$ is the same as or different than M;

L represents the organic sulfone compound;

b and c are positive numbers that, together with d, reflect an electrostatically neutral complex;

d is zero or a positive number;

x and y are numbers that reflect an electrostatically neutral salt;

r is from 4 to 6; t is from 0 to 2; and z, a and n are positive numbers indicating the relative quantities of organic sulfone compound, water and $M^3_xA_y$, respectively.

4. The catalyst of claim 2, wherein each $R^5$ is a 1–4 carbon atom alkyl group.

5. The catalyst of claim 2, wherein the $R^5$ groups together form a 5–8 member ring with the sulfur atom of the sulfone groups.

6. The catalyst of claim 3 wherein M and $M^3$ are zinc ions, $M^1$ is a cobalt ion, t is zero, d is zero, A is chloride ion, x is one and y is two.

7. The catalyst of claim 3 wherein M and $M^3$ are zinc ions, $M^1(CN)_r(X)_t$ is a mixture of hexacyanocobaltate and nitroferricyanide ions, d is zero, A is chloride ion, x is one and y is two.

8. The catalyst of claim 1 which is complexed with an organic sulfoxide compound represented by the general structure $R^5$—S(O)—$R^5$ wherein each $R^5$ is independently an unsubstituted or inertly substituted alkyl, cycloalkyl, aryl group, or, together with the other $R^5$, forms part of a ring structure that includes the sulfur atom of the sulfoxide group.

9. The catalyst of claim 8 wherein the metal cyanide catalyst is represented by the general structure

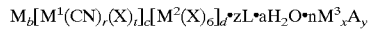

wherein

M is a metal ion that forms an insoluble precipitate with the $M^1(CN)_r(X)_t$ group and which has at least one water soluble salt;

$M^1$ and $M^2$ are transition metal ions that may be the same or different;

each X independently represents a group other than cyanide that coordinates with an $M^1$ or $M^2$ ion;

$M^3_xA_y$ represents a water-soluble salt of metal ion $M^3$ and anion A, wherein $M^3$ is the same as or different than M;

L represents the organic sulfone compound;

b and c are positive numbers that, together with d, reflect an electrostatically neutral complex;

d is zero or a positive number;

x and y are numbers that reflect an electrostatically neutral salt;

r is from 4 to 6; t is from 0 to 2; and z, a and n are positive numbers indicating the relative quantities of organic sulfoxide compound, water and $M^3_xA_y$, respectively.

10. The catalyst of claim 9, wherein each $R^5$ is an 1–4 carbon atom alkyl group.

11. The catalyst of claim 9, wherein the $R^5$ groups together form a 5–8 member ring with the sulfur atom of the sulfoxide group.

12. The catalyst of claim 9 wherein M and $M^3$ are zinc ions, $M^1$ is a cobalt ion, t is zero, d is zero, A is chloride ion, x is one and y is two.

13. The catalyst of claim 9 wherein M and $M^3$ are zinc ions, $M^1(CN)_r(X)_t$ is a mixture of hexacyanocobaltate and nitroferricyanide ions, d is zero, A is chloride ion, x is one and y is two.

14. In a process for polymerizing an epoxide compound in the presence of a catalyst and an initiator compound, the improvement wherein the catalyst is a metal cyanide catalyst complexed with an organic sulfone or sulfoxide compound.

15. The process of claim 14, wherein the epoxide compound is propylene oxide or a mixture of propylene oxide and ethylene oxide.

16. The process of claim 15, wherein the product is a polyether polyol having a hydroxyl equivalent weight of at least 1000 and an unsaturation content of less than 0.02 meq/g.

* * * * *